United States Patent [19]

Digenis et al.

[11] Patent Number: 5,032,402
[45] Date of Patent: Jul. 16, 1991

[54] 3-HYDROXY-N-METHYLPYRROLIDONE AND USE AS TRANSDERMAL ENHANCER

[75] Inventors: George A. Digenis; Walter J. Doll; Amale Hawi, all of Lexington, Ky.

[73] Assignee: The University of Kentucky Research Foundation, Lexington, Ky.

[21] Appl. No.: 554,501

[22] Filed: Jul. 19, 1990

Related U.S. Application Data

[62] Division of Ser. No. 263,384, Oct. 27, 1988, Pat. No. 4,973,708.

[51] Int. Cl.$^5$ .............................................. A61F 13/02
[52] U.S. Cl. .................................... 424/448; 424/449; 514/946; 514/947
[58] Field of Search ................ 424/449, 448; 514/946, 514/947

[56] References Cited

U.S. PATENT DOCUMENTS 4,039,664  8/1977  Stoughton ............................ 424/180
4,537,776  8/1985  Cooper .................................. 514/424
4,568,343  2/1986  Leeper .................................. 604/896

Primary Examiner—Thurman Page
Assistant Examiner—D. Gabrielle Phelan
Attorney, Agent, or Firm—Lowe, Price, LeBlanc & Becker

[57] ABSTRACT

The novel compound, 3-hydroxy-N-methylpyrrolidone, is effective as a transdermal enhancer for the absorption of drugs through the skin of humans and animals. The 3-hydroxy-N-methylpyrrolidone is prepared from delta-butyrolactone which is converted to methyl 2,4-dibromobutyrate, this intermediate is reacted with methylamine to form N-methyl-2,4-dibromobutyramide, this intermediate is converted to 3-bromo-N-methyl-2-pyrrolidone by ring closure, and the 3-bromo-N-methyl-2-pyrrolidone is reacted with an alkaline earth metal carbonate or alkaline metal carbonate to form 3-hydroxy-N-methyl-2-pyrrolidone.

3 Claims, 3 Drawing Sheets

3-HYDROXY-N-METHYLPYRROLIDONE AND USE AS TRANSDERMAL ENHANCER

This is a division of application Ser. No. 07/263,384 filed Oct. 27, 1988, now U.S. Pat. No. 4,973,708, dated Nov. 27, 1990.

TECHNICAL FIELD

This invention relates to a new composition for drug delivery and more particularly relates to use of the compound 3-hydroxy-N-methylpyrrolidone as a transdermal enhancer for the absorption of drugs into humans and animals by absorption through the skin.

BACKGROUND ART

Transdermal absorption is currently one of the fastest growing methods of drug delivery. Transdermal therapeutic systems are self-contained dosage forms that, when applied to intact skin, deliver drug(s) at a controlled rate to the systemic circulation. Advantages of using the transdermal route include: enhanced therapeutic efficacy, reduction in the frequency of dosing, reduction of side effects due to optimization of the blood-concentration versus time profile, increased patient compliance due to elimination of multiple dosing schedules, bypassing the hepatic "first-pass" metabolism, avoiding gastrointestinal incompatibilities and providing a predictable and extended duration of activity. However, the main function of the skin is to act as a barrier to entering compounds. As a consequence, transdermal therapy has so far been restricted to a limited number of drugs that possess the desirable physiochemical properties for diffusion across the skin barrier. One effective method of overcoming the barrier function of the skin is to include a penetration enhancer in the formulation of a transdermal therapeutic system. See Barry, Brian W.: *Dermatological Formulations: Percutaneous Absorption* (Dekker, New York, 1983); Bronough et al, *Percutaneous Absorption, Mechanisms-Methodology-Drug Delivery*, (Marcel Dekker, New York, N. Y. 1985); and Monkhouse et al, Transdermal drug delivery-problems and promises. *Drug Dev. Ind. Pharm.*, 14, 183-209 (1988).

A penetration enhancer is a chemical compound that, when included in a formulation, temporarily increases the permeability of the skin to the drug allowing more of the drug to be absorbed in a shorter period of time. Several different types of penetration enhancers have been reported such as dimethylsulfoxide, n-decyl methyl sulfoxide, N,N-dimethylacetamide, N,N-dimethylformamide, 1-dodecylazacycloheptan-2-one (Azone), propylene glycol, ethanol, pyrrolidones such as N-methyl-2-pyrrolidone (NMP) and surfactants. See Bronough et al, supra, and Stoughton et al, Azone: A New Non-toxic enhancer of percutaneous penetration. *Drug Dev. Ind. Pharm.*, 9, 725-744 (1983).

N-methyl-2-pyrrolidone is a versatile solvent which is miscible with water, ethyl alcohol, ether, chloroform, benzene, ethyl acetate and carbon disulfide. N-methylpyrrolidone has been widely used as a solvent in industrial processes such as petroleum refining, GAF Corp.: "M-Pyrol (N-methyl-2-pyrrolidone) Handbook.", GAF Corp., New York, 1972. It is currently used as a solubilizing agent in topical and parenteral veterinary pharmaceuticals and is now under consideration for use in products intended for humans, Wells, D.A. et al: Disposition and Metabolism of Double-Labeled [$^3$H and $^{14}$C] N-methyl-2-pyrrolidone in the Rat. *Drug Met. Disps.*, 16, 243-249 (1988). Animal and human experiments have shown very little irritation or sensitization potential. Ames type assays and chronic exposure studies have not revealed any significant toxicity, Wells et al, Mutagenicity and Cytotoxicity of N-methyl-2-pyrrolidone and 4-(methyl amino) Butanoic Acid in the Salmonella/microsome Assay. *J. Appl. Tox.*, 8, 135-139 (1988). N-methylpyrrolidone has also been shown to be an effective penetration enhancer. Barry et al, Optimization of Bioavailability of Topical Steroids: Penetration Enhancers Under Occlusion. *J. Inv. Derm.*, 82, 49-52 (1984); Akter et al, Absorption Through Human Skin of Ibuprofen and Flurbiprofen; Effect of Dose Variation, Deposited Drug Films, Occlusion and the Penetration Enhancer N-methyl-2-pyrrolidone. *J. Pharm. Pharmacol.*, 37, 27-37 (1984); Holegaard et al, Vehicle Effect on Topical Drug Delivery IV. Effect of N-methylpyrrolidone and Polar Lipids on Percutaneous Transport. *Int. J. Pharm.*, 43, 233-240 (1988); Sugibayashi et al, Effect of Several Penetration Enhancers on the Percutaneous Absorption of Indomethacin in Hairless Rat. *Chem. Pharm. Bull.*, 36, 1519-1528 (1988); Bennett et al, Optimization of Bioavailability of Topical Steroids: Non-Occluded penetration Enhancers Under Thermodynamic Control. *J. Pharm. Pharmacol.*, 37, 298-304 (1985); Sasaki et al, Enhancing Effect of Pyrrolidone Derivatives on Transdermal Drug Delivery. 1. *Int. J. Pharm.*, 44, 15-24 (1988); Lee et al, Toxicity of N-methyl-2-pyrrolidone (NMP): Tetratogenic, Subchronic and Two-Year Inhalation Studies, *Fund. Appl. Tox.*, 9, 222-235 (1987).

There remains a need in the art of transdermal delivery for a penetration enhancer which is safe, effective, and provides advantages not known to penetration enhancers of the prior art.

DISCLOSURE OF THE INVENTION

It is accordingly one object of the present invention to provide a novel penetration enhancer for use in transdermal drug delivery.

A further object of the present invention is to provide as a novel chemical compound, 3-hydroxy-N-methylpyrrolidone having advantageous characteristics as a penetration enhancer in transdermal delivery systems.

A further object of the invention is to provide methods for preparation of the novel penetration enhancer, 3-hydroxy-N-methylpyrrolidone.

A still further object of the present invention is to provide transdermal delivery systems which contain as a safe and effective penetration enhancer, 3-hydroxy-N-methylpyrrolidone.

Other objects and advantages of the present invention will become apparent as the description thereof proceeds.

In satisfaction of the foregoing objects and advantages, there is provided by this invention a novel penetration enhancing compound, 3-hydroxy-N-methylpyrrolidone.

There is also provided by this invention a method for preparation of 3-hydroxy-N-methylpyrrolidone which comprises conversion of delta-butyrolactone to methyl-2,4-dibromobutyrate, conversion of the methyl-2,4-dibromobutyrate to N-methyl-2,4-dibromobutyramide, ring closure of the N-methyl-2,4-dibromobutyramide to form 3-bromo-N-methyl-2-pyrrolidone, and conversion of the 3-bromo-N-methyl-2-pyrrolidone to 3-hydroxy- N-methyl-2-pyrrolidone by reaction with alkali metal carbonate.

The present invention also provides transdermal compositions comprising as the penetration enhancer, 3-hydroxy-N-methyl-2-pyrrolidone. The present invention also provides a method for delivery of drugs through the human skin which comprises preparation of a transdermal drug delivery system containing 3-hydroxy-N-methylpyrrolidone as a penetration enhancer, and applying the transdermal composition to the human skin.

BRIEF DESCRIPTION OF DRAWINGS

Reference is now made to the accompanying drawings wherein.

BEST MODE FOR CARRYING OUT THE INVENTION

Figure 1:
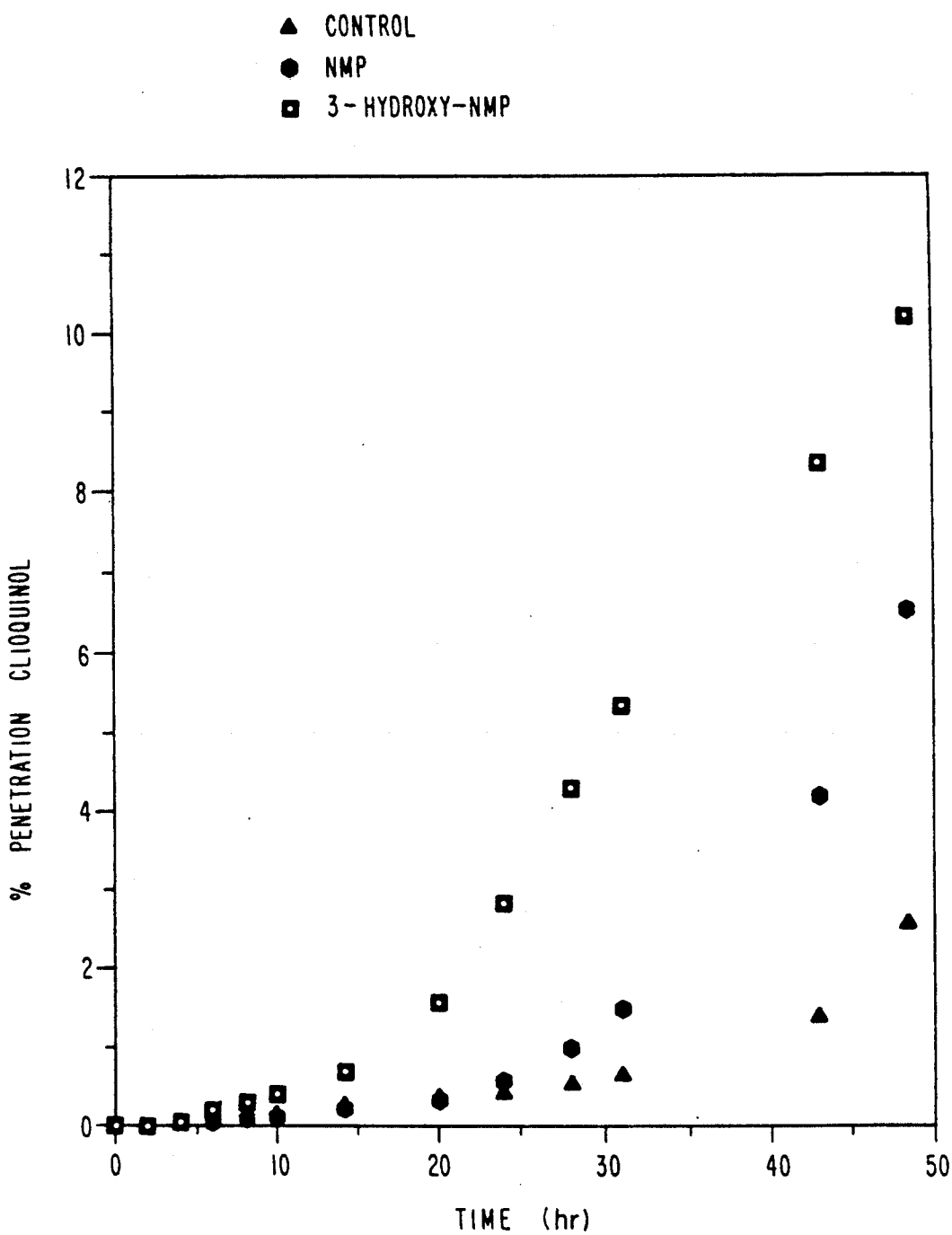
FIG. 1 is a graph showing a comparison of the percent penetration of $^{131}$I-labeled Clioquinol when delivered with 3-hydroxy-N-methylpyrrolidone, N-methylpyrrolidone, and without an enhancer.

It has been discovered according to this invention that 3-hydroxy-N-methylpyrrolidone, also known as 3-hydroxy-N-methyl-2-pyrrolidone, is an effective penetration enhancer when used in transdermal drug delivery systems. 3-hydroxy-N-methylpyrrolidone is a novel compound prepared according to methods described herein. In general, the compound is a white solid having a melting point of 71°-72° C. and is of the following structural formula:

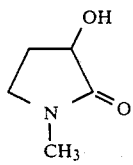

This novel compound is prepared through a series of novel chemical steps, preferably using as the basic starting material delta-butyrolactone. In a preferred procedure, delta-butyrolactone is reacted with bromine in the presence of a bromide compound such as phosphorus tribromide and under an elevated temperature in the range of 75°-125° C. In a preferred procedure, the bromide compound and delta-butyrolactone are mixed with agitation and at an elevated temperature, liquid bromine is slowly added. The temperature may be controlled in the preferred range by the rate of addition of the bromine and by external heating. Preferably the amount of bromine added to the butyrolactone is in the molecular ratio of about 1:2. Bromine addition is stopped when HBr evolution becomes evident, after which the reaction mixture is cooled and combined with methanol. The resulting solution is then saturated with HCl gas, the methanol is removed and methyl-2,4-dibromobutyrate is removed as a pale yellow liquid.

In a second step of the reaction, the methyl-2,4-dibromobutyrate is reacted with methylamine in an aqueous solution at a temperature of below ambient in order to form N-methyl-2,4-dibromobutyramide. Then butyramide is then recovered and purified to obtain the solid intermediate product.

The N-methyl-2,4-dibromobutyramide is then converted to 3-bromo-N-methyl-2-pyrrolidone by reaction with alkali metal alkoxide to effect ring closure. In this reaction, an alcoholic solution of the N-methyl2,4-dibromobutyramide is formed and freshly prepared alkali metal alkoxide, preferably sodium ethoxide, is added drop-wise to the mixture under an inert atmosphere. After the reaction is complete, the mixture is filtered and the alcohol removed under reduced pressure. This solid intermediate is then purified to provide a yellow liquid intermediate product.

The recovered 3-bromo-N-methyl-2-pyrrolidone is then converted to the 3-hydroxy-N-methyl-2-pyrrolidone of this invention by reaction with an alkali metal or alkaline earth metal carbonate in a substantially stoichiometric reaction and in an aqueous medium. Preferably the reactant is added to a solution of the 3-bromo-N-methyl-2-pyrrolidone under agitation and while heating in the range of 75°-125° C. After the reaction is complete, the 3-hydroxy-N-methylpyrrolidine white solid product is recovered and purified.

The following is a schematic showing this four-step reaction.

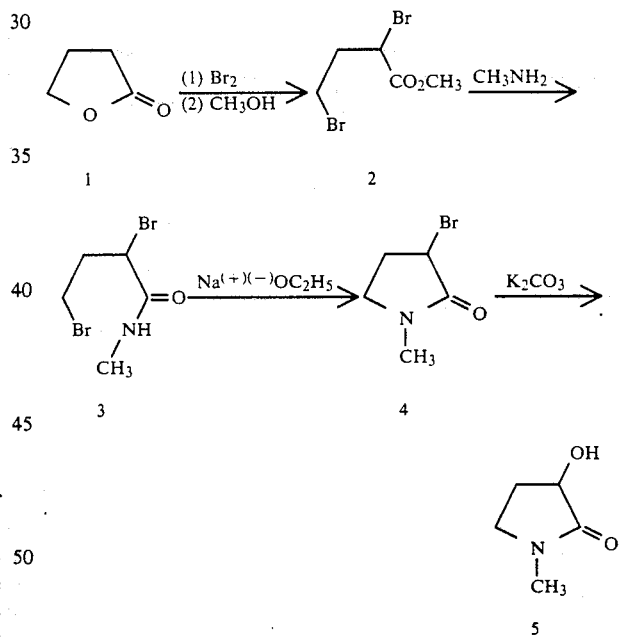

As pointed out above, a penetration enhancer is a chemical compound which, when included in a transdermal formulation, affects the skin of a human by increasing permeability of the skin to allow more of a drug to be absorbed in a shorter period of time. The penetration enhancer is normally contained in a formulation, called a transdermal composition, in combination with the appropriate drug to be delivered and other known components of the formulation. According to this invention, it has been discovered that the 3-hydroxy-N-methylpyrrolidone provides unexpectedly improved effects as a penetration enhancer when incorporated into a transdermal formulation. As mentioned herein, N-methylpyrrolidone is a known penetration enhancer. In studies leading to this invention using the prior art compound, N-methyl-2-pyrrolidone, it was discovered that a major metabolite of N-methylpyrrolidone which is excreted in the urine is 3-hydroxy-N-methyl-2-pyrrolidone. The subsequent synthesis of this compound, and closer examination of physical properties of the compound, led to the present discovery that 3-hydroxy-N-methylpyrrolidone possesses several advantages over similar compounds such as N-methylpyrrolidone as a penetration enhancer. Thus, 3-hydroxy-N-methylpyrrolidone provides at least equal and often superior enhancement of transdermal absorption while exposing the body to a lower metabolic burden. Further, 3-hydroxy-N-methylpyrrolidone is a "softer" xenobiotic to the body because no energy will be expended in metabolic processes after the compound's absorption into the systemic circulation. Also, in view of the apparent safety of N-methylpyrrolidone, its major metabolite, 3-hydroxy-N-methylpyrrolidone, would be expected to have an even lower toxicity.

The 3-hydroxy-N-methylpyrrolidone of this invention may be used as the penetration enhancer in any transdermal drug delivery system in which it is effective. It is considered that the 3-hydroxy-N-methylpyrrolidone is compatible with all known drugs which are systematically active and can be delivered in a transdermal system to be absorbed by the body surface. As is known, a transdermal delivery system comprises or reservoir for the composition to be transferred including the drug of choice, the carrier, and the penetration enhancer. In general, the reservoir will be contained between a backing member and a pressure-sensitive adhesive which enables the transdermal device to be applied to the skin. Transdermal delivery systems are well known in the art and described, for example, in U. S. Pat. Nos. 3,598,122, 3,797,494, and 4,230,105. It is considered according to the present invention that the penetration enhancer of this invention can be used in all such systems.

In practicing this invention one can employ any systemically active drug which will be absorbed by the body surface to which the transdermal bandage is applied, consistent with their known dosages and uses. Of course, the amount of drug necessary to obtain the desired therapeutic effect will vary depending on the particular drug used. Suitable systemic drugs include, without limitation, Anti-microbial agents such as penicillin and tetracycline; Sedatives and Hypnotics such as pentabarbital sodium and phenobarbital; Psychic Energizers such as 3-(2-aminopropyl) indole acetate; tranquilizers such as reserpine, chloropromazine hydrochloride, and thiopropazate hydrochloride; Hormones; Antipyretics such as aspirin, salicylamide, and sodium salicylate; morphine and other narcotic analgesics; Antidiabetics, e.g., insulin; Cardiovascular Agents, e.g., nitroglycerin, and cardiac glycosides such as digitoxin, Anti-spasmodics such as atropine, and methscololamine bromide; Anti-malarials such as the 4-aminoquinolines; and Nutritional Agents such as vitamins, essential amino acids, and essential fats.

Further, topically active drugs consistent with their known dosages and uses can be administered. Suitable drugs include without limitation: Antiperspirants, e.g., aluminum chloride; Deodorants, e.g., hexachlorophene, Astringents, e.g., tannic acid; Irritants, e.g., methyl salicylate, Keratolytics, e.g., benzoic acid; Antifungal Agents; Anti-inflammatory Agents; Anti-neoplastic Agents, And Antibacterial Agents.

The above and other drugs can be present in the reservoir alone or in combination form with pharmaceutical carriers. The pharmaceutical carriers acceptable for the purpose of this invention are the art known carriers that do not adversely affect the drug, the host, or the material comprising the drug delivery device. Suitable pharmaceutical carriers include sterile water; saline, dextrose; dextrose in water or saline; condensation products of castor oil and ethylene oxide combining about 30 to about 35 moles of ethylene oxide per mole of castor oil; liquid glyceryl triester of a lower molecular weight fatty acid; lower alkanols; oils such as corn oil; peanut oil, sesame oil and the like, with emulsifiers such as mono-or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also contain adjuvants such as preserving, stabilizing, wetting, emulsifying agents and the like together with the penetration enhancer of this invention.

The following examples are presented to illustrate the invention. However, it is not to be considered as limited thereto. In the examples and through the specification, parts are by weight unless otherwise indicated.

EXAMPLE 1

Synthesis of 3-hydroxy-N-methyl-2-Pyrrolidone

General. Melting points were determined on a Fisher-Johns melting point apparatus and are uncorrected. H-NMR and C-NMR spectra were obtained using a Varian Gemini 200MHz or Varian XL-300 300 MHz spectrometer. Mass spectra were run on a Kratos MS50 TA mass spectrometer with. a KratosDS90 data system. Infrared (IR) spectra were recorded on a Perkin-Elmer Ratio Recording spectrophotometer. Microanalysis were performed by Atlantic Microlab, Inc., Atlanta, Ga.

Reactions were routinely followed by thin layer chromatography (TLC) using Whatman K6F silica gel plates. Spots were visualized by exposure to iodine vapor or uv lamp (254 nm). Column chromatography was carried out using silica gel (Davidson Chemical, Baltimore, Md.).

Materials. Delta-Butyrolactone (Aldrich, Cat. No. B10,360-8, lot 2710BK, 99%), Bromine (J. T. Baker, Cat. No. 1-9760, lot 849381), Phosphorous tribromide (Aldrich, Cat. No. 25,653-6, lot 1413BM), methanol (Fisher, Cat. No. A-412, lot 854027), Methylamine, 40 wt % solution in water (Aldrich, Cat. No. M2,775-1, lot 03804CT), absolute ethanol (Midwest Solvents Company of Ill.), potassium carbonate (Aldrich, Cat. No. 20,961-9, lot 04006BP, 99+%).

A. Methyl 2,4-dibromobutyrate. Phosphorous tribromide (2.0 ml, 5.7 gm, 0.021 mole) was added to deltabutyrolactone (100.8 gm, 1.17 mole) and the mixture was heated to 100° C. while stirring. Bromine (30 ml, 93.4 gm, 0.59 mole) was slowly added dropwise beneath the surface of the liquid. The temperature was controlled at 110°–115° C. by the rate of addition of bromine and an oil bath. Additional PBr$_3$ (1.0 ml, 2.85 gm, 0.011 mole) was added to the reaction vessel and bromine addition was then continued until HBr evolution was evident (approx. 25 ml, 80 gm, 0.49 mole). The reaction mixture was stirred and cooled to room temperature and finally cooled in an ice bath. The mixture was combined with methanol (480 ml) and the resulting solution was saturated with HCl gas. The solution was allowed to stand overnight at room temperature after which the methanol was removed under reduced pressure. The residue was dissolved in ether, washed with 5% sodium bicarbonate solution, dried over magnesium sulfate and filtered. The solvent was removed and the residue distilled under reduced pressure to yield a clear pale yellow liquid, 2 (216.4 gm, 71%); b.p. 80°–85° C. @ 2–3 mm of Hg, IR(neat) 1775, 1735, 1470 and 1380–1130 cm$^{-1}$; H-NMR (CDCl$_3$) δ 2.54 (q, 2H, -CH$_2$-CHBr-), 3.55 (t, 2H, Br-CH$_2$-CH$_2$-), 3.81 (s, 3H, O-CH$_3$), 4.56 (t, 1H, -CH$_2$-CHBr-); C-NMR, decoupled (CDCl$_3$) 29.60, 36.69, 43.24, 53.10, 169.77 ppm. Anal. calcd. for C$_5$H$_8$O$_2$Br$_2$ (295.934): C, 23.10; H, 3.10. Found: C, 23.39; H, 3.14%.

B. N-Methyl-2,4-dibromobutyramide. Methyl 2,4-dibromobutyrate (50 gm, 0.192 mole) was mixed with 40 wt % methylamine in aqueous solution (20.0 ml, 7.22 gm, 0.232 mole) with stirring and cooling in an ice bath. The reaction mixture was stirred for 16 hours at 5° C., chloroform (100 ml) was then added and the organic layer washed with water. The organic extract was dried over magnesium sulfate, filtered and the solvent removed. The crude product was purified by column chromatography (silica gel, gradient elution hexane/chloroform to chloroform/ethylacetate) to yield an off-white solid, (25.4 gm, 51.7%): m.p. 42°–47° C. The compound was used in the next step without further purification. A small portion was further purified for elemental analysis; m.p. 48°–49° C. IR(KBr) 3450, 1660, 1570, 1415, 1240 and 1210 cm$^{-1}$; H-NMR (CDCl$_3$) δ2.48 (m, 1H, -CH$_2$-CHBr-), 2.79(m, 1H, -CH$_2$-CHBy-), (d, 3H, -NH$_2$-CH$_3$-), 3.55 (t, 2H, Br-CH$_2$-CH$_2$), 4.54 (dd, 1H, -CHBr-); 6.39 (s, broad, 1H, -NH-CH$_3$), C-NMR, decoupled (CDCl$_3$) 26.83, 30.27, 37.60, 48.26, 168.65 ppm. Anal. calcd. for C$_5$H$_9$NBr$_2$O (258.949): C, 23.19; H, 3.50; N, 5.41. Found: C, 23.53; H, 3.44; N, 5.29%.

C. 3-Bromo-N-methyl-2-pyrrolidone. To a stirred solution of N-methyl-2,4-dibromobutyramide (25.9 gm, 0.1 mole) in 65 ml of dry ethanol, kept under nitrogen, was added dropwise an equimolar quantity of freshly prepared sodium ethoxide (2.3 gm Na in 50 ml ethanol) over 40 minutes. After two hours the mixture was filtered and the ethanol removed under reduced pressure. The residue was dissolved in chloroform and washed with water, then washed with saturated aqueous NaCl. Removal of the solvent and distillation under reduced pressure yielded a yellow liquid, (11.55 gm, 65.2%); b.p. 90°–94° C. @ 0.1–1 mm. IR(neat) 1700, 1495, 1440, 1405 and 1300 cm$^{-1}$; H-NMR (CDCl$_3$) δ 2.32 (m, 1H, -CH$_2$-CHBr-), 2.72 (sextet, 1H, -CH$_2$-CHBr-), 2.90 (s, 3H, -N-CH$_3$), 3.32 (m, 1H, N-CH$_2$-CH$_2$-), 3.58 (m, 1H, N-CH$_2$-CH$_2$-), 4.42 (dd, 1H, -CH$_2$-CHBr-); C-NMR, decoupled (CDCl$_3$) 33.6, 35.1, 44.2, 47.5, 171.5 ppm. Anal. calcd. for C$_5$H$_8$BrNO (178.03): C, 33.73; H, 4.53; N, 7.87. Found: C, 33.81; H, 4.52; N, 7.82%.

D. 3-Hydroxy-N-methyl-2-pyrrolidone -3-Bromo-N-methyl-2-pyrrolidone (2.0 gm, 0.011 mole) was dissolved in 100 ml of purified water. Potassium carbonate (2.33 gm, 0.017 mole) was added while stirring and the mixture was heated to 100°–110° C. After 4 hours, the reaction mixture was poured onto ice and neutralized with 1% aqueous HCl. Water was removed under reduced pressure and the residue extracted with boiling 95% ethanol. After removal of the solvent, the product was purified by column chromatography (silica gel, gradient elution using from chloroform to chloroform/ethylacetate/methanol) to yield a white solid, (0.754 gm, 58.5%); m.p. 71°–72° C. IR(nujol) 3120(broad), 1670, 1400, 1305, 1270 and 1170 cm$^{31}$ $^1$; H-NMR (CDCl$_3$) δ 1.98 (m, 1H, -CH$_2$-CHOH-), 2.41 (m, 1H, -CH$_2$-CHOH-), 2.84 (s, 3H, -N-CH$_3$), 3.30 (m, 2H, -CH$_2$-N-), 4.30 (triplet of doublets, 1H, -CH-OH), 5.18 (d, 1H, -CH-OH), C-NMR, decoupled (CDCl$_3$) 27.38, -CH$_2$-CHOH-), 29.74 (-N-CH$_3$), 45.74 (-CH$_2$-N-), 69.41 (-CH-OH-), 175.53 -CHOH-CO-N-) ppm. Partially decoupled and 2-dimensional HETCOR spectra support the assignments as given. Anal. calcd. for C$_5$H$_9$NO$_2$ (115.129): C, 52.16; H, 7.88; N, 12.17%. Ms(70eV) - Extract molecular ion M+ calculated for 115.06332, Found: 115.0634. Fragmentation pattern: 86 (M-29); 54 (M-58); 42 (M-73).

EXAMPLE 2

Radioiodination of 5-chloro-8-hydroxy-iodoquinoline.

This example prepares the radioiodinated control, 5-chloro-8-hydroxy-iodoquinoline to be used in tests described hereinafter to determine the effect of penetration of the 3-hydroxy-N-methylpyrrolidone of this invention.

Materials. Sodium Iodide-125 (New England Nuclear NEZ 033, radiochemical and radionuclidic purity 99%), Sodium iodide-131 (New England Nuclear NEZ 035H, radiochemical and radionuclidic purity 99%), 5-chloro-8-hydroxy quinoline hydrochloride (Aldrich, lot 3128LJ Cat No. 25,044-9), 5-chloro-8-hydroxy-7iodoquinoline (Aldrich, lot 0513KL Cat. No. 22,406-5), Iodobeads (Pierce Chemical Company No. 28666).

Synthesis of 5-chloro-8-hydroxy-7[$^{125}$I]-Iodoquinoline. An aqueous solution (0.1N NaOH) containing approximately one mCi of Na$^{125}$I was diluted to 0.5 ml with methanol. Three iodobeads were added and the solution was left to stand for 5 minutes at room temperature. 5-Chloro-8-hydroxyquinoline (0.5 ml of a stock solution containing 200 ug/ml in methanol) was added and the reaction vessel was shaken occasionally for 30 minutes. The iodobeads were then removed, 5-chloro-8-hydroxy-7-iodoquinoline (5.0 ml of a stock solution containing 1 mg/ml in methanol) was added followed by 20.0 ml of purified water. The resulting white precipitate was filtered and washed with water until the filtrate activity was at background levels. The product was then dissolved in CH$_2$CL$_2$ (10 ml), transferred to a 25 ml pear shaped flask and the solvent removed under reduced pressure. Assay by uv spectroscopy at 256 nm showed that 4.84 mg of 5-chloro-8-hydroxy-7-iodoquinoline were recovered. Specific activity approximately 120 uCi/mg.

Synthesis of 5-chloro-8-hydroxy-7-[$^{131}$I]-Iodoquinoline. This compound was prepared by the same procedure described above using Na$^{131}$I.

Assessment of Radiochemical Purity. Analysis and identification of radiolabeled 5-chloro-8-hydroxy-7-iodoquinoline and determination of radiochemical purity was performed by HPLC. The HPLC system used consisted of the following components: isocratic pump (Altex model 110A, Berkley, Calif.), fixed volume injector (Rheodyne model 7125, Cotari, Calif.), Waters u-Bondapak TM C-18 reverse phase column (Waters Ass., Milford, Mass.), uv detector (Waters model 440, Milford, Mass.), Radiomatic Model ES stream splitter (Radiomatic Instruments and Chemicals, Tampa, Fla.), Radiomatic Model HP flow-through radioactivity detector (Radiomatic Instruments and Chemicals, Tampa, Fla.), dual channel strip chart recorder (Linear Instruments Inc., model 858, Irvine, Calif.).

Samples were introduced using a 50ul fixed volume injection loop. A mobile phase containing 70% methanol (Fisher HPLC grade, lot 874675) and 30% 0.05M phosphoric acid (Eastman, lot 620) was filtered using a 0.22u filter, degassed under vacuum and delivered at a flow rate of 1.0 ml/min. After passing through the column, the mobile phase effluent passed through the uv detector set at 254 nm and was split by the stream splitter. A percentage of the effluent was sent to the flow through radioactivity detector and the remainder diverted to waste. This detector mixed scintillation coctail (Scintiverse LC, Fisher) with the effluent in a ratio of 4:1 (v/v). The uv output was recorded on one channel of the strip chart recorder and the radioactivity output was recorded simultaneously on the second channel.

Standards were prepared by dissolving 5.0 mg of unlabeled 5-chloro-8-hydroxy-7-iodoquinoline or 5.0 mg of 5-chloro-8-hydroxyquinoline in 100 ml of mobile phase to make a final concentration of 50 ug/ml. Radioactive samples were prepared by dissolving the reaction product (4.84 mg) in methanol, taking a small aliquot (100 ul), evaporating and reconstituting in mobile phase.

Figure 3:
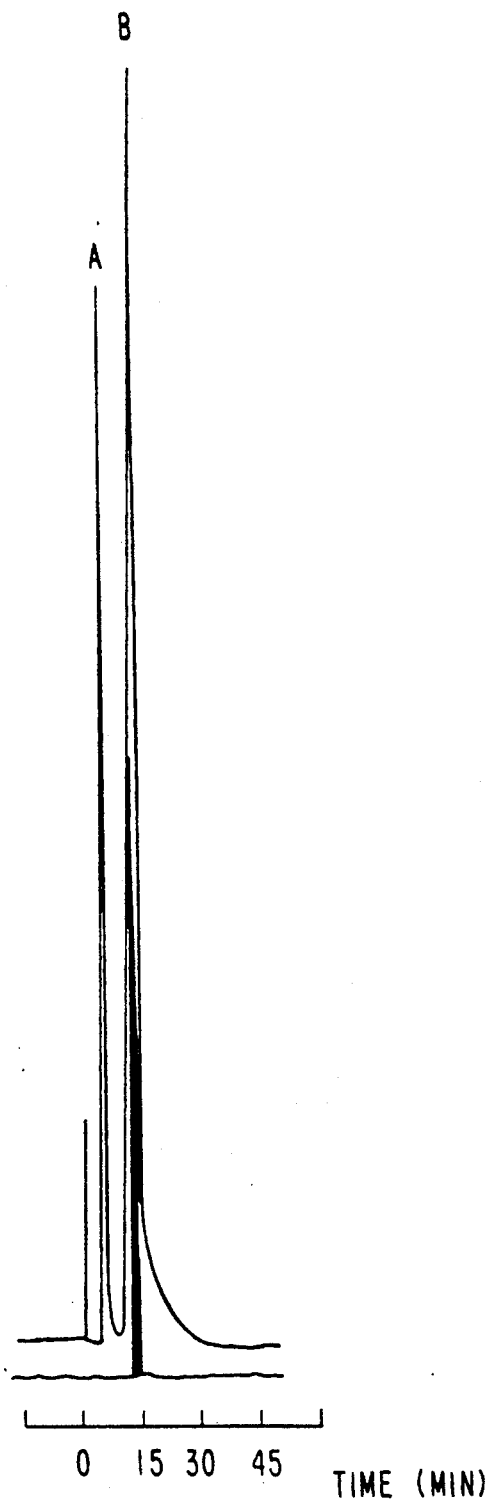
FIG. 3 is an HPLC radiochromatogram of the 5-chloro-8-hydroxy-7-[$^{131}$I]-iodoquinoline, the drug chosen to test the penetration enhancing characteristics of the compound of the invention.

The retention time for 5-chloro-8-hydroxy-7-iodoquinoline was 10.5 minutes. 5-chloro-8-hydroxyquinoline eluted with the solvent front at 3 minutes. An HPLC chromatogram for 5-chloro-8-hydroxy-7-[$^{131}$I]-iodoquinoline is shown in FIG. 3. In FIG. 3, the upper tracing represents UV detection of radioiodination product at 254 nm; A: solvent front/ 5-chloro-8-hydroxyquinoline, B: 5-chloro-8-hydroxy-7-iodoquinoline. Lower tracing represents radioactivity detection which was monitored continuously using a flow through liquid scintillation counter. Only one radioactive peak (lower tracing) was detected that corresponds to the uv peak of 5-chloro-8-hydroxy-7-iodoquinoline.

EXAMPLE 3

In vitro penetration of radioiodinated 5-chloro-8-hydroxy-7-iodoquinoline.

General. Standard Franz diffusion cells (15 mm i.d., O-ring design) were manufactured by Crown Glass Inc., Somerville, N. J. The cell caps were modified with ground glass joints to fit 14/20 ground glass stoppers. A Franz diffusion cell drive consol F-DCD-9 was also manufactured by Crown Glass. A Vandercamp 2500 recirculating water bath was used to maintain the cells at 37° C. Split thickness human allograph tissues (0.015 in. thickness), thigh back area, was obtained from the Tissue Transplant Bank, St. Agnes Medical Center, Philadelphia, Pa. Samples were counted in a Packard Auto-Gamma Scintillation Spectrometer.

Materials. Sterile Saline (0.9% Sodium Chloride USP, Travenol, NDC 0338-0049-04 lot co56747), Albumin (Bovine, fraction v, Sigma A-4503 lot 127F-0877), N-Methyl-2-pyrrolidone (Aldrich 99+% Cat No. 24,279-9 lot 04402TP), Neomycin Sulfate (Sigma N-1876 lot 66F-0151), absolute ethanol (Midwest Solvents Company of Ill.).

Procedure. Human allograph tissue, which had been stored at −70° C., was thawed and immediately mounted in a Franz type diffusion cell. The receptor chamber was filled with normal saline containing 2% albumin and 0.05% neomycin sulfate. Each cell was maintained at 37° C. and stirred at 600 rpm. After the cells had been allowed to equilibrate for 4 to 6 hours, 200 ul of a saturated ethanolic solution of 5-chloro-8-hydroxy-7-[$^{125}$I]-iodoquinoline (approx. 70 uCi, 0.44 mg) was applied to the donor side of each cell. This was immediately followed by either 200 $\mu$l of absolute ethanol for the control cells, 200 $\mu$l of 50% (w/v 3-hydroxy-N-methylpyrrolidone in ethanol or an equimolar ethanolic solution of N-methylpyrrolidone (43.1% w/v). The cells were then capped with ground glass stoppers. At various time intervals, over an 80–100 hour period, the entire contents of the receptor chamber was removed with a 10cc syringe and placed into a vial. The receptor chamber was then refilled with fresh solution. After the last collection these vials were placed in a well-type gamma counter and counted for I-125 activity.

At the time of dosing 200 $\mu$l of the saturated 5-chloro-8-hydroxy-7-[$^{125}$I]-iodoquinoline solution was placed into separate vials to calculate the amount of activity (dose) applied to the skin.

EXAMPLE 4

In this example, 3-hydroxy-N-methyl pyrrolidone was tested for its use as a percutaneous penetration enhancer. In vitro studies were carried out using Franz type diffusion cells. The penetration enhancing properties of 3-hydroxy-N-methylpyrrolidone was compared to N-methyl pyrrolidone, a compound known to enhance the penetration of drugs through the skin.

For these in vitro studies radioiodinated 5-chloro-8-hydroxy-7-iodoquinoline was chosen as a model drug. This drug, known as Clioquinol USP, is currently marketed by Ciba (Ciba Pharmaceutical Company, 556 Morris Avenue, Summit, N. J. 07901), as a topical antibacterial/antifungal agent tradenamed Vioform TM. It was chosen because 1) it is a drug that is absorbed very slowly through the skin and 2) Clioquinol inherently has iodine in its structure, allowing easy preparation of a radiolabeled analogue. This radiolabeled marker is conveniently used to follow the penetration of the drug through the skin.

Franz diffusion cells are designed to mimic in vivo conditions. A finite dose of drug is applied to the stratum corneum side of the skin and penetration is followed by analyzing for the drug in the receptor phase underneath. In these studies the amount of drug crossing the skin barrier is estimated by counting total radioactivity in the receptor phase. While no excised tissue has been found to duplicate in vivo absorption in humans, excised human skin is generally regarded as the best substitute and was therefore used in these studies.

In a preliminary study, the transdermal absorption of Clioquinol was evaluated in the presence of 3-hydroxy-N-methylpyrrolidone, N-methylpyrrolidone, and in the absence of enhancer. An ethanolic solution of [I-131]-Clioquinol was applied to 3 cells followed by either ethanol (control), 50% 3-hydroxy-N-methyl-pyrrolidone in ethanol or an equimolar solution of N-methylpyrrolidone. In FIG. 1, the percent penetration of 5-chloro-8-hydroxy-7-[$^{131}$I]-iodoquinoline through human skin is illustrated. The amount of 5-chloro-8-hydroxy-7-[$^{131}$I]-iodoquinoline activity applied is equal to 100%. As shown in FIG. 1, the extent of enhancement by 3-hydroxy-N-methyl-pyrrolidone is clearly evident. At 48.5 hours the amount of I-131 Clioquinol that had penetrated through the skin in the presence of 3-hydroxy-N-methyl-pyrrolidone (10.2% absorbed) was 3.9 times greater than the control (2.6% absorbed) and 1.5 times more than with N-methylpyrrolidone (6.5% absorbed).

Figure 2:
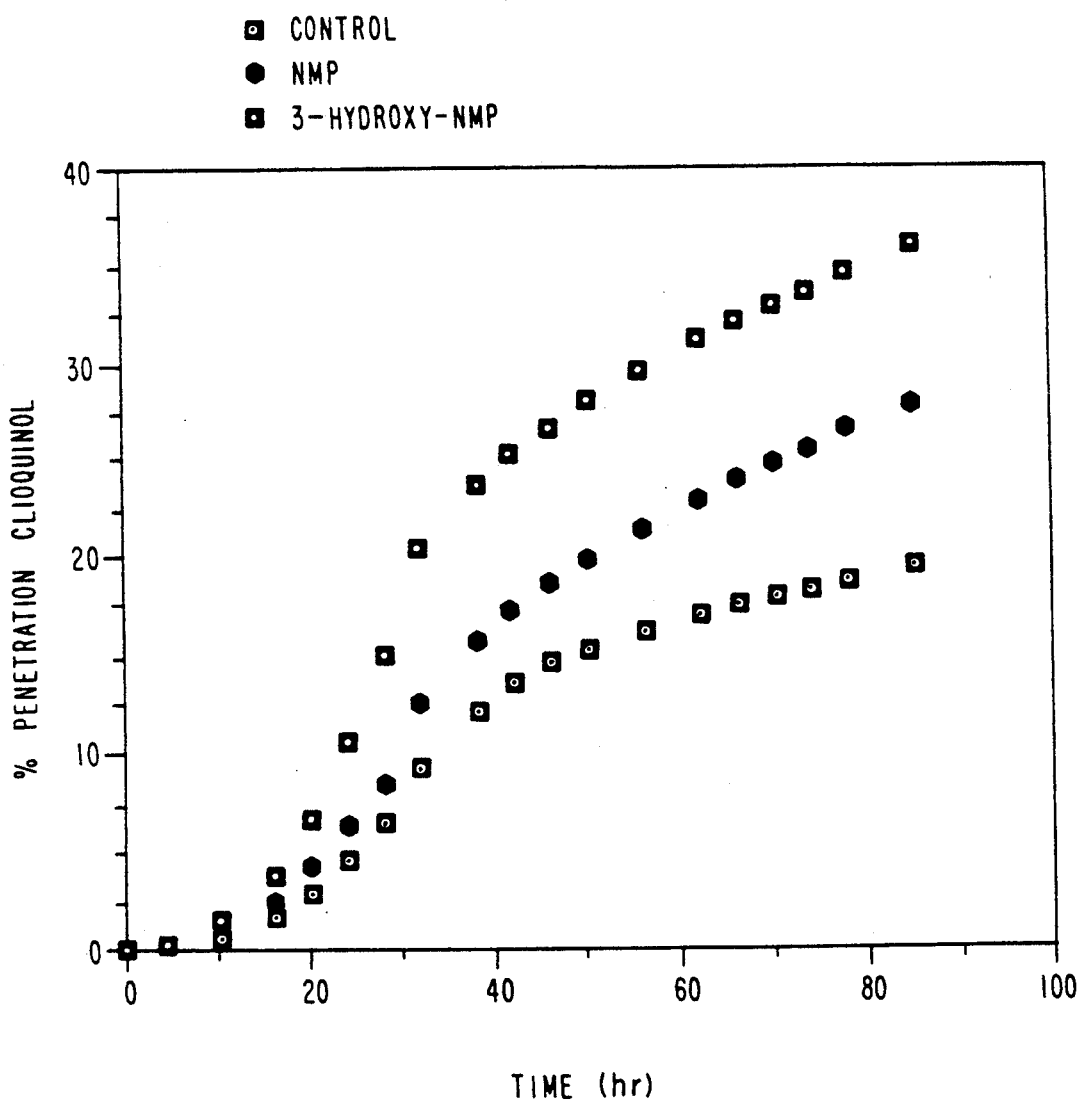
FIG. 2 is a graph showing the percent penetration of $^{125}$I-labeled Clioquinol using 3-hydroxy-N-methylpyrrolidone, N-methylpyrrolidone, and without an enhancer.

The study was repeated using I-125 labeled Clioquinol. Iodine-125 was used because the longer half-life ($t_{\frac{1}{2}}=60d$) and lower energy gamma ray (0.035 Mev) were better suited to our experimental design. The results are shown in FIG. 2. In FIG. 2, the percent penetration of 5-chloro-8-hydroxy-7-[$^{125}$I]-iodoquinoline through the human skin is illustrated. The amount of 5-chloro-8-hydroxy-7[$^{125}$I]-iodoquinoline applied is equal to 100%. The relative order of enhancement was found to be the same with 3-hydroxy-N-methylpyrrolone>N-methylpyrrolone>control. The amount of Clioquinol penetrating the skin in the presence of 3-hydroxy-N-methylpyrrolidone (40.0% absorbed) was 1.8 times higher than the control (19.5% absorbed) and 1.3 times greater than with N-methyl-pyrrolidone (27.8% absorbed ) at 85.5 hours. Alternatively, the same amount of Clioquinol was absorbed in approximately 32 hours in the presence of 3-hydroxy-N-methylpyrrolidone (19% absorbed) as was absorbed in 85 hours in the absence of 3-hydroxy-N-methylpyrrolidone.

The results of these experiments indicate that 3-hydroxy-N-methylpyrrolidone shows great potential for use as a percutaneous penetration enhancer. The absorption of Clioquinol was clearly increased in the presence of 3-hydroxy-N-methylpyrrolidone as compared to its absorption in the presence of ethanol and N-methylpyrrolidone. In addition, since 3-hydroxy-N-methylpyrrolidone is a major metabolite of N-methylpyrrolidone, it should offer the advantage of being a lower toxicological burden to the body.

The mechanism by which penetration enhancers exert their effects has not been clearly established. Possible modes of action that have been suggested include altering membrane fluidity in the stratum corneum, altering the partitioning behavior of the drug between the stratum corneum and the underlying dermal tissues and solubilizing the lipid components of the stratum corneum. Most likely penetration enhancers work by a combination of these and other mechanisms with one mechanism being more dominant than others for a particular type of enhancer. Although the mechanism is not known, since 3-hydroxy-N-methylpyrrolidone effectively enhances the absorption of a poorly absorbed compound like Clioquinol, this suggests that 3-hydroxy-N-methylpyrrolidone will be effective for enhancing the percutaneous absorption of many other poorly absorbed compounds.

In conclusion, a novel compound, 3-hydroxy-N-methylpyrrolidone, was synthesized and was shown to effectively enhance the in-vitro absorption of a model drug. Further, 3-hydroxy-N-methylpyrrolidone is shown to be more effective than N-methylpyrrolidone in enhancing the absorption of drugs. Because it is a metabolite, 3-hydroxy-N-methylpyrrolidone should be metabolically softer to the body and less irritating than other compounds such as N-methylpyrrolidone. The introduction of a potent, non-toxic and non-irritating compound that can effectively enhance the penetration of poorly absorbed drugs would open the way for the clinical use of transdermal therapeutic systems containing drugs that otherwise could not be administered by this route.

The invention has been described herein with reference to certain preferred embodiments. However, as obvious variations thereon will become apparent to those skilled in the art, the invention is not to be considered as limited thereto.

We claim:

1. An article of manufacture for the continuous administration of drugs by absorption through the skin which comprises as a penetration enhancer for the drug, 3-hydroxy-N-methylpyrrolidone.

2. An article of manufacture according to claim 1 wherein the article of manufacture comprises a reservoir for the drug and the penetration enhancer, a backing member, and a pressure-sensitive adhesive for application of the article to the skin.

3. A method for the administration of drugs through the human skin which comprises preparation of a drug delivery system which contains the drug and as a penetration enhancer, 3-hydroxy-N-methylpyrrolidone, and applying the composition to the human skin.

* * * * *